United States Patent [19]

Ogawa

[11]  4,266,534
[45]  May 12, 1981

[54] ILLUMINATION UNIT FOR ENDOSCOPE

[75] Inventor: Mototugu Ogawa, Chofu, Japan

[73] Assignee: Olympus Optical Co., Ltd., Tokyo, Japan

[21] Appl. No.: 38,577

[22] Filed: May 14, 1979

Related U.S. Application Data

[63] Continuation-in-part of Ser. No. 944,324, Sep. 21, 1978, abandoned.

[30] Foreign Application Priority Data

Oct. 8, 1977 [JP]  Japan ................................. 52/135697

[51] Int. Cl.³ ............................................... A61B 1/06
[52] U.S. Cl. ............................................. 128/6; 128/23;
350/437; 362/336; 362/32
[58] Field of Search ................................. 128/3-9,
128/23; 350/96.26, 194, 197, 175 LD, 188;
356/241; 362/32, 335, 336, 337, 338, DIG. 804,
16, 17, 18

[56]  References Cited

U.S. PATENT DOCUMENTS

| 2,072,849 | 3/1937 | Dietrich | 350/194 |
| 2,796,800 | 6/1957 | Klemperer et al. | 350/194 |
| 2,878,721 | 3/1959 | Kanolt | 350/194 |
| 3,309,162 | 3/1967 | Kosanke et al. | 350/194 |

FOREIGN PATENT DOCUMENTS

| 53-5471 | 8/1978 | Japan . | |
| 53-101482 | 8/1978 | Japan . | |
| 964567 | 7/1964 | United Kingdom | 350/96.26 |

*Primary Examiner*—Robert W. Michell
*Assistant Examiner*—Arthur S. Rose
*Attorney, Agent, or Firm*—Weinstein & Sutton

[57]  ABSTRACT

An illuminating unit for endoscopes includes a light guide member and a cover glass disposed forwardly of the light exiting end face of the light guide member and located within an illumination window which is formed in the distal end of the endoscope. The cover glass has an entry and an exit surface through which light passes, at least one of said surfaces being formed with a surface configuration comprised of a plurality of coaxial concave lens portions having different radii of curvature, each concave coaxial lens portion having a radius of curvature which is less than that of the surrounding lens portion.

The aforesaid surface configuration may be formed upon either the entry or exit surface of the cover glass or both of said surfaces. In the two former cases, the remaining one of the entry and exit surfaces may be provided with a concave lens surface having a uniform radius of curvature.

14 Claims, 4 Drawing Figures

ILLUMINATION UNIT FOR ENDOSCOPE

BACKGROUND OF THE INVENTION

This application is a continuation-in-part of application Ser. No. 944,324 filed Sept. 21, 1978, now abandoned.

The invention relates to an illumination unit for an endoscope, and more particularly, to such unit of the type having a cover glass located within an illumination window and through which illuminating light transmitted through a light guide disposed within a flexible tube of an endoscope exits.

In the conventional arrangement of illumination unit for an endoscope of the type described, the cover glass is located forwardly of the end face of the light guide from which light exits. The said cover glass is disposed in a water-tight manner within an illumination window which is mounted at the distal end of the endoscope. The cover glass is often formed with a concave lens portion in order to increase the illumination angle of exiting light rays.

One example of such arrangement is illustrated in FIG. 1. Cover glass 1 is tightly fitted into illumination window 103 formed at the distal end 102 of an endoscope so as to form a water-tight seal with the window. Light guide member 104, which comprises a bundle of optical fibres, has its exposed end face 104a disposed centrally in the bottom of illumination window 103. Illuminating light is provided from an external source (typically located at the proximal end of the guide member 104). Light transmitted through light guide member 104 exits from the end face 104a and is directed into a coeloma through cover glass 101. The inner surface of cover glass 101, namely, the surface which is in direct opposition to end face 104a, is defined by concave lens 105 having a uniform radius of curvature. The concave lens 105 increases the area which can be illuminated by the light exiting the window 103 as a result of the refraction illustrated in FIG. 1 which occurs as the light passes through the cover glass. However, it will be seen from FIG. 1 that because concave lens 105 is formed as part of a spherical surface, rays b impinging on the central region of the lens will be refracted by an amount which is less than the refraction which rays impinging on the peripheral region of the lens experiences (illustrated by rays a). Thus, the exiting rays b from the central region cannot be spread as desired. Consequently, although satisfactory brightness is obtained in the central region of the field of sight of the endoscope, the conventional endoscopes of the prior art fail to achieve a uniform and sufficient brightness over the entire field.

SUMMARY OF THE INVENTION

It is an object of the invention to provide an illumination unit for an endoscope which is capable of providing uniform and sufficient brightness over the entire field of sight, by forming the concave lens of the cover glass with a plurality of coaxial concave lens portions having different radii of curvature.

In accordance with the invention all of the preferred embodiments have at least one lens surface formed of a plurality of concave lens portions having different radii of curvature formed in a cover glass which is disposed forwardly of a light exiting end face of light guide member which transmits the illuminating light. This arrangement permits a greater degree of refraction for rays passing through the central region to achieve a satisfactory diffusion so that the level of brightness of the peripheral region can be maintained at substantially the same level as the central region of the field of sight. In this manner, simple means can be used to facilitate an observation of the interior of a coeloma.

The aforesaid arrangement may be provided upon either the light entry or light exit surface of the cover glass or upon both the entry or exit surfaces. As a further alternative one of said entry or exit surfaces may have the novel concave lens configuration while the remaining surface may have a concave lens surface having a uniform radius of curvature.

DESCRIPTION OF PREFERRED EMBODIMENTS

Figure 1:
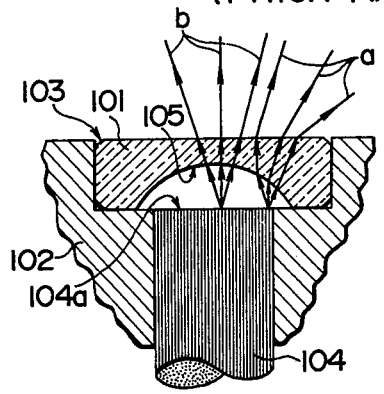
FIG. 1 is an enlarged cross section of a cover glass of a conventional illumination unit.
Figure 2:
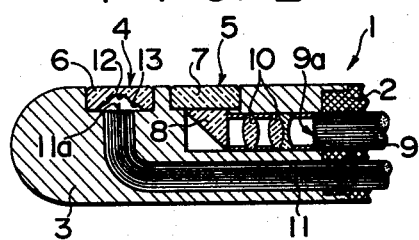
FIG. 2 is a fragmentary cross section of the illumination unit according to one embodiment of the invention.

Referring to FIG. 2, there is shown endoscope 1 including flexible tube 2, the distal end 3 of which is adpated to be inserted into a coeloma. Illumination window 4 and observation window 5 are formed in the sidewall of the distal end and are adjacent to each other. Transparent cover glasses 6, 7 are fitted into the respective windows 4, 5 in a water-tight manner and are secured against movement.

Right-angled prism 8 is disposed below cover glass 7 and is in close contact with the bottom surface thereof. Objective lens system 10 is disposed between prism 8 and the distal end of an image guide member 9, which extends through flexible tube 2 of the endoscope. The member 9 comprises a bundle of optical fibres. A light image which is incident on observation window 5 is refracted by prism 8 and is focussed by objective lens system 10 onto the distal end face 9a of member 9. The focussed image can be observed through guide member 9 and a magnifying glass (not shown) which is disposed in the controller of the endoscope which is located outside of the coeloma.

Light guide member 11, which also comprises a bundle of optical fibres, extends through the flexible tube 2 and has its end face 11a exposed centrally in the bottom surface of illumination window 4. Illuminating light introduced into guide member 11 from an external source exits the end face 11a and passes through cover glass 6 to be directed toward a coeloma.

Figure 3:
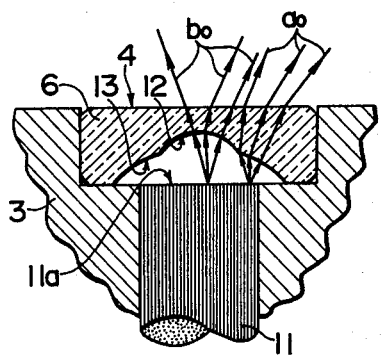
FIG. 3 is an enlarged cross section of the cover glass shown in FIG. 2.

As shown in FIG. 3, the entry surface of cover glass 6 is provided with a plurality of coaxial concave lens portions, which are two in number in the present embodiment as indicated at 12 and 13, having different radii of curvature, the centers of the imaginary circles formed by said radii being located on a common axis A. The lens portions are formed in the entry surface of cover glass 6 which is disposed in direct opposition to end face 11a. The inner lens portion 12 has a radius of curvature which is less than that of the concentric outer concave lens portion 13 so that rays impinging on lens portion 12 experience a greater degree of refraction as they pass through cover glass 6.

As illustrated at $b_0$, the exiting rays which pass through the flat exit surface of ground glass 6 will be sufficiently spread outside cover glass 6. Illuminating light impinging on the peripheral region of cover glass 6 will be refracted by the outer concave lens portion 13, the exiting rays $a_0$ being also spread outside cover glass 6. As a consequence, the light which illuminates the coeloma exhibits an increased brightness in the peripheral region of the field of the sight even though the brightness in the central region will be slightly reduced as compared with the conventional arrangement, thereby achieving a uniform brightness over the entire field.

Figure 4:
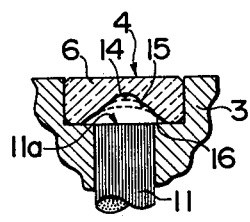
FIGS. 4 through 8 are enlarged cross sections of other preferred embodiments of the cover glass.

FIG. 4 shows the use of three coaxial concave lens portions 14, 15 and 16 on the entry surface of the ground glass said lens portions having the centers of their radii of curvature arranged on a common axis, with the innermost lens portion having a radius of curvature which is less than that of the concentric middle lens portion, and the outermost concentric lens portion having the largest radius of curvature.

Figure 5:
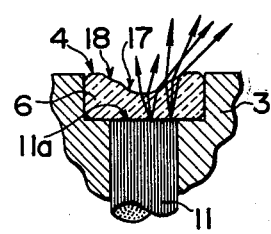

Instead of forming the entry surface of the cover glass so as to define the concave lens portions, the outer, light exiting surface of cover glass 6 may be defined by concave lens portions 17, 18 having different radii of curvature as illustrated in FIG. 5. This achieves an effect upon exiting light rays which is similar to that of the embodiments shown in FIGS. 3 and 4.

Figure 6:
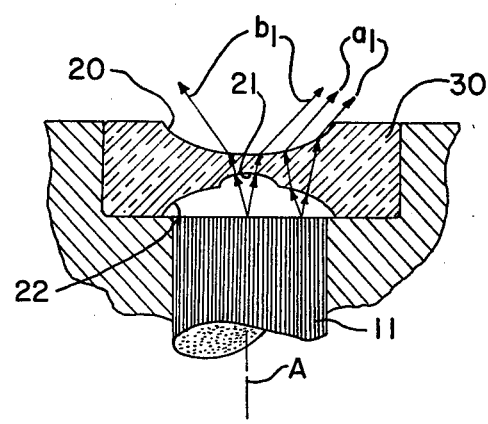

FIG. 6 shows another preferred embodiment of the present invention in which the entry surface of cover glass 30 has a concave lens comprised of lens surface portions 21 and 22 substantially the same as the entry surface shown in FIG. 3. The exit surface is provided with a concave lens surface 20 having a single uniform radius of curvature. The center of the circle defining the curved surface 20 preferably lies on the same axis A as the centers of the imaginary circles defining the concave lens portions of entry surface 22. The spread angle of rays $b_1$ entering concave lens portion 21 and leaving the cover glass in the central region of concave lens surface 20 is larger than the spread angle of rays $b_0$ leaving the exit surface in the central region of the cover glass 6 of FIG. 3. This increased spread angle is due to the light refraction at concave central lens surface 21 along the entry surface of the cover glass and the light refraction at concave lens surface 20 along the exit surface 6 of the cover glass 30.

Figure 7:
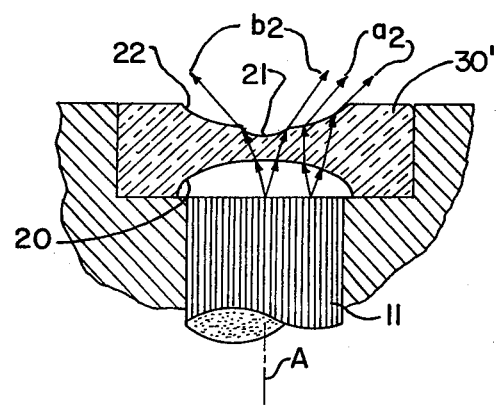

The cover glass embodiment 30' of FIG. 7 is basically identical to that shown in FIG. 6 except that the concave lens surfaces 20 and 21–22 are respectively arranged upon the entry and exit surfaces of the cover glass. The resulting spread angle of rays $b_2$ entering lens surface 20 and exiting lens surface 21 is substantially the same as that obtained from the embodiment of FIG. 6 and provides a spread angle in the central region which is larger than that spread angle of the rays $b_0$ passing through the concave surface 12 in the embodiment of FIG. 5.

Figure 8:
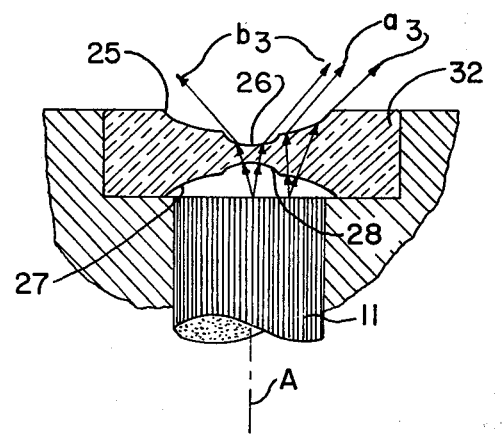

FIG. 8 shows still another embodiment of cover glass 32 in which both the entry and exit surfaces of the cover glass are provided with coaxial concave lens surfaces of the type shown in FIG. 3. The spread angle of rays $b_3$ entering concave surface portion 28 and leaving concave surface portion 26 is still further improved over the spread angles obtained in any of the previously described embodiments. The choice of embodiments described herein is thus dependent upon the size of the field of view over which more uniform brightness is desired.

It is to be understood that the concave surface of respective lens portions need not be part of a true spherical surface, but may be formed to be an approximation of part of a spherical surface. The centers of radii of curvature of the individual concave lens portions on either the same side or on opposite sides of the cover glass need not be in complete alignment, but may be offset from each other depending on the area of the field of sight of the endoscope. While the above described embodiments illustrate the use of the invention with an endoscope of lateral view type, it may be similarly applied to an endoscope of direct view type.

A latitude of modification, change and substitution is intended in the foregoing disclosure and, in some instances, some features of the invention will be employed without a corresponding use of other features. Accordingly, it is appropriate that the appended claims be construed broadly in a manner consistent with the spirit and scope of the invention herein.

What is claimed is:

1. An illumination unit for an endoscope comprising a light guide member disposed within a flexible tube of an endoscope for transmitting illumination light that is introduced into the light guide member to an illuminating window provided in the endoscope, a cover glass disposed forwardly of a light exiting end face of the light guide member and located within the illumination window formed at the distal end of the endoscope for directing the illuminating light into a coeloma as the light exits the end face of said light guide member, said cover glass having an entry and an exit surface, at least one of said surfaces having a plurality of substantially concentrically disposed concave lens portions having different radii of curvature to refract the light emitted from the exit surface of the cover glass to a greater degree toward the outer concentric portion thereof than toward the central portion of the cover glass to spread the light illumination over a larger field of view.

2. An illumination unit according to claim 1 in which the plurality of concave lens portions are arranged on the entry surface of the cover glass which is the surface of said cover glass which is closer to the light exiting end face of said light guide member.

3. An illumination unit according to claim 1 in which the plurality of concave lens portions are arranged on the exit surface of the cover glass which is the surface of the cover glass further removed from the exit face of said light guide member.

4. An illumination unit according to claim 1 in which the light guide member comprises a bundle of optical fibres.

5. The illumination unit of claim 1 wherein said light guide member has a first end remote from said illuminating window for receiving light whereby the light guide member guides the received light toward the exiting end face, which is substantially flat.

6. An illumination unit for an endoscope comprising a flexible tube having a first end, a light guide member disposed within said tube for transmitting illuminating light to the first end of said tube, said first end having an illuminating window, a cover glass having light entry and light exiting surfaces positioned within the illuminating window and adapted to pass light entering its entry surface from said light guide member outwardly through said window and said exit surface into the area to be illuminated, one of said surfaces of said cover glass through which said light is transmitted having a concave central lens portion and a concave lens portion surrounding said central lens portion, said central lens portion having a surface curvature which differs from the surface curvature of the concave lens portion of the cover glass surrounding said central lens portion wherein said concave lens portions cooperate to refract the light emitted from the light exiting surface of the cover glass to a greater degree toward the outer concentric portion thereof than toward the central portion of the cover glass to spread the light illumination over a larger field of view and thereby provide a wide illumination area of substantially uniform light intensity.

7. The illumination unit of claim 6 wherein the remaining surface of said cover glass opposite said one surface is provided with a central portion with a surface curvature which differs from the surface curvature of the portion of the cover glass surrounding said central portion wherein said surface curvatures cooperate to provide a wide illumination area of substantially uniform light intensity.

8. The illumination unit of claim 7 wherein the centers of the imaginary circles defining said concave lens portions lie on a common central axis.

9. The illumination unit of claim 7 wherein said one surface of said cover glass is arranged so as to be directly opposite the adjacent end of said light guide member.

10. The illumination unit of claim 6 wherein the remaining surface of said cover glass is provided with a concave lens surface having a uniform radius of curvature.

11. The illumination unit of claim 10 wherein the centers of the imaginary circles defining said concave central lens portion and the concave lens surface respectively provided on opposite surfaces of said cover glass lie on a common central axis.

12. The illumination unit of claim 10 wherein said one surface of said cover glass is arranged to be directly opposite the adjacent end of said light guide member.

13. The illumination unit of claim 10 wherein said remaining surface of said cover glass is arranged to be immediately opposite the adjacent end of said light guide member.

14. An illumination unit for an endoscope comprising a light guide member disposed within a flexible tube of an endoscope for transmitting illuminating light that is introduced into the light guide member to an illuminating window provided in the endoscope, a cover glass disposed forwardly of a light exiting face of the light guide member and located within the illumination window formed at the distal end of the endoscope for directing the illuminating light into a coeloma as it exits the end face of said light guide member, said cover glass having entry and exit surfaces through which light rays pass, a central portion of said cover glass and a portion surrounding said central portion respectively having first means having a curvature and second means having a curvature different from said first curvature means such that the first curvature means refracts the major portion of light rays passing through said central portion by an amount greater than the refraction experienced by light rays passing through the portion of said cover glass surrounding said central portion so that the spread angle of the major portion of light rays passing out of said exit surface in said central lens portion is greater than the spread angle of light rays passing out of the portion of the exit surface surrounding said central portion to thereby spread the light illumination over a larger field of view.

* * * * *